United States Patent
Kelm et al.

(10) Patent No.: US 9,642,586 B2
(45) Date of Patent: May 9, 2017

(54) COMPUTER-AIDED ANALYSIS OF MEDICAL IMAGES

(71) Applicants: Michael Kelm, Erlangen (DE); Yefeng Zheng, Dayton, NJ (US)

(72) Inventors: Michael Kelm, Erlangen (DE); Yefeng Zheng, Dayton, NJ (US)

(73) Assignee: Siemens Aktiengesellschaft, München (DE)

( * ) Notice: Subject to any disclaimer, the term of this patent is extended or adjusted under 35 U.S.C. 154(b) by 234 days.

(21) Appl. No.: 14/462,014

(22) Filed: Aug. 18, 2014

(65) Prior Publication Data

US 2016/0045180 A1 Feb. 18, 2016

(51) Int. Cl.
*G06K 9/00* (2006.01)
*A61B 6/00* (2006.01)
(Continued)

(52) U.S. Cl.
CPC .......... *A61B 6/5235* (2013.01); *A61B 5/7267* (2013.01); *A61B 6/032* (2013.01);
(Continued)

(58) Field of Classification Search
CPC . G06T 2207/30101; G06T 2207/30048; G06T 7/0012; G06T 7/0022
(Continued)

(56) References Cited

U.S. PATENT DOCUMENTS

| 6,047,080 A * | 4/2000 | Chen .................... G06T 11/006 382/128 |
| 7,397,935 B2 * | 7/2008 | Kimmel ................ G06T 7/0081 382/128 |

(Continued)

FOREIGN PATENT DOCUMENTS

| JP | 2009195586 A | 9/2009 |
| JP | 2010011980 A | 1/2010 |

(Continued)

OTHER PUBLICATIONS

Breiman, L., "Random Forests," Machine Learning, 45(1), pp. 5-32, 2001.
(Continued)

*Primary Examiner* — Yosef Kassa
(74) *Attorney, Agent, or Firm* — Lempia Summerfield Katz LLC

(57) ABSTRACT

A pair of medical images is analyzed, the pair including a first image, which is a contrasted scan of a part in a human or animal body, and a second image, which is a native scan of the same part of the human or animal body. Anatomic structures are identified within both the first image and the second image. By using those anatomic structures, centerlines of vessels in the first image are mapped to the second image. Candidate calcified plaques are extracted in the second image, and calcified plaques out of the candidate calcified plaques are identified by a machine learning classifier. The positional information of the centerlines in the second image is used for extracting the candidate calcified plaques in the second image and/or for identifying the calcified plaques out of the candidate calcified plaques by the machine learning classifier.

20 Claims, 2 Drawing Sheets

(51) Int. Cl.
*A61B 5/00* (2006.01)
*A61B 6/03* (2006.01)
*G06T 7/00* (2017.01)

(52) U.S. Cl.
CPC .............. *A61B 6/503* (2013.01); *A61B 6/504* (2013.01); *A61B 6/508* (2013.01); *A61B 6/5217* (2013.01); *G06T 7/0012* (2013.01); *G06T 7/0081* (2013.01); *G06T 7/0097* (2013.01); *G06T 2207/10081* (2013.01); *G06T 2207/30101* (2013.01); *G06T 2207/30172* (2013.01)

(58) Field of Classification Search
USPC ............... 382/128, 130, 131, 132, 155, 159; 128/922, 923
See application file for complete search history.

(56) References Cited

U.S. PATENT DOCUMENTS

| | | | |
|---|---|---|---|
| 7,627,156 B2* | 12/2009 | Margolis | A61B 5/02007 382/128 |
| 7,773,792 B2* | 8/2010 | Kimmel | G06T 7/0081 382/128 |
| 8,092,483 B2* | 1/2012 | Galdonik | A61M 25/0138 606/200 |
| 8,137,904 B2* | 3/2012 | Szalay | A61K 35/545 424/9.1 |
| 8,290,228 B2* | 10/2012 | Cohen | G06T 7/0022 382/128 |
| 8,463,007 B2* | 6/2013 | Steinberg | G06T 7/0022 378/4 |
| 8,512,311 B2* | 8/2013 | Strauss | A61K 38/18 604/500 |
| 8,526,699 B2* | 9/2013 | Mittal | G06T 7/0016 382/131 |
| 8,653,756 B2* | 2/2014 | Szczeszynski | H05B 33/0815 315/185 R |
| 8,670,603 B2* | 3/2014 | Tolkowsky | G06T 7/0022 382/130 |
| 8,958,618 B2 | 2/2015 | Masood et al. | |
| 9,259,199 B2 | 2/2016 | Yao et al. | |
| 2011/0118595 A1 | 5/2011 | Aulbach et al. | |
| 2012/0300903 A1 | 11/2012 | Yao et al. | |
| 2014/0003701 A1 | 1/2014 | Masood et al. | |

FOREIGN PATENT DOCUMENTS

| | | |
|---|---|---|
| JP | 2012245351 A | 12/2012 |
| JP | 2014008402 A | 1/2014 |

OTHER PUBLICATIONS

Isgum, I., et al., "Detection of coronary calcifications from computed tomography scans for automated risk assessment of coronary artery disease," Med. Phys. 34 (4), pp. 1450-1461, 2007.

Kelm, B., et al., "Detection, Grading and Classification of Coronary Stenoses in Computed Tomography Angiography," In: Proc. MICCAI, pp. 1-8, 2011.

Zheng, Y., et al., "Four-Chamber Heart Modeling and Automatic Segmentation for 3D Cardiac CT Volumes Using Marginal Space Learning and Steerable Features," IEEE Trans. Med. Imaging 27(11), pp. 1-14, 2008.

Zheng, Y., et al., "Robust and Accurate Coronary Artery Centerline Extraction in CTA by Combining Model-Driven and Data-Driven Approaches," In: Proc. MICCAI, pp. 1-8, 2013.

Zheng, Y., et al., "Fast and Automatic Heart Isolation in 3D CT Volumes: Optimal Shape Initialization," In: Proc. Intl. Workshop on Machine Learning in Medical Imaging (In conjunction with MICCAI), pp. 1-8, 2010.

Zheng, Y., "Pericardium Based Model Fusion of CT and Non-Contrasted C-arm CT for Visual Guidance in Cardiac Interventions," In: Proc. MICCAI, pp. 1-8, 2014.

European Search Report for related European Application No. 15178891.6 dated Apr. 4, 2016.

Japanese Search Report for related Japanese Application No. 2015-161175, dated Nov. 9, 2016.

Kelm, B. Michael, and Yefeng Zheng. "Automatic Coronary Calcium Scoring Using Native and Contrasted CT Acquisitions." MICCAI Challenge on Automatic Coronary Calcium Scoring (2014): 1-8.

Saur, Stefan C., et al. "Automatic detection of calcified coronary plaques in computed tomography data sets." Medical Image Computing and Computer-Assisted Intervention—MICCAI 2008. Springer Berlin Heidelberg, 2008. 170-177.

* cited by examiner

COMPUTER-AIDED ANALYSIS OF MEDICAL IMAGES

BACKGROUND

The present embodiments relate to a method for computer-aided analysis of medical images as well as to a corresponding apparatus.

Calcified plaques in vessels (particularly arteries) are detected by analyzing medical images. Based on the detected calcified plaques, a physician can perform a diagnosis of a patient in order to reveal artery diseases. Particularly for cardiac medical images, the detection of calcified plaques is very important for a subsequent diagnosis of diseases and particularly for diagnosing coronary artery disease.

In most clinical tools, a semi-automatic approach is used for detecting calcified plaques in arteries. To do so, groups of voxels in 3D CT scans being potential candidates for calcified plaques are automatically identified. The identified groups of voxels are then manually assigned to specific vessels in order to distinguish the coronary calcium inside vessels from bone, calcium outside of vessels, and noise.

SUMMARY AND DESCRIPTION

The scope of the present invention is defined solely by the appended claims and is not affected to any degree by the statements within this summary.

A method and an apparatus for computer-aided analysis of medical images enable an automatic detection of calcified plaques within vessels.

A pair of medical images are analyzed, where said pair includes a first image that is a contrasted scan of a part in a human or animal body (i.e. a scan made after injecting a contrast agent in the human or animal body) and a second image that is a native scan of the same part of the human or animal body without contrast agent. The native scan is usually taken before the contrasted scan. This is because the contrast agent remains a certain time in the human and animal body, thus not enabling a native scan. In one embodiment of a method, the following acts a) to e) are performed.

In an act a), one or more anatomic structures are identified within both the first image and the second image, resulting in a positional information of the one or more anatomic structures in the first and second images.

In an act b), first centerlines of vessels and particularly arteries in the first image are identified, resulting in a positional information of the first centerlines in the first image.

In an act c), second centerlines of vessels in the second image corresponding to respective first centerlines in the first image are identified, resulting in a positional information of the second centerlines in the second image. In this act c), the identification of the second centerlines includes the step of mapping the first centerlines from the first image to the second image by estimating a spatial transform from the first image to the second image based on the identified one or more anatomic structures in the first and second images.

Thereafter, candidate calcified plaques are extracted in the second image in an act d), and calcified plaques out of the candidate calcified plaques are identified by a machine learning classifier (i.e., a classifier learned by a computer-implemented machine learning method). This machine learning classifier processes a number of features of the candidate calcified plaques. The above mentioned act d) and/or act e) uses the positional information of the second centerlines in the second image that has been determined in act c).

Vessels can be extracted more accurately in contrasted scans than in native scans. However, calcified plaques can be found easier in native scans. By processing both scans and using the positional information of identified centerlines of vessels, a fast, accurate and automatic computer-implemented detection of calcified plaques belonging to vessels can be achieved.

In a particularly preferred embodiment, the medical images being processed are three-dimensional scans and/or CT scans (CT=computer tomography). Particularly, three-dimensional CT scans are processed. However, the method may also be used for MRT scans and particularly 3D MRT scans (MRT=Magnetic Resonance Tomography).

The detection of calcified plaques is particularly important in coronary arteries. Hence, in a preferred embodiment, the medical images are scans of a human or animal heart wherein the identified first and second centerlines of vessels refer to coronary arteries.

When analyzing medical images of a human or animal heart, the one or more anatomic structures identified in act a) preferably include the pericardium and/or the aortic root in the human or animal heart.

For identifying the anatomic structures, well-known prior art methods can be used. In a particularly preferred embodiment, marginal space learning is used for this identification. Known prior art methods may also be used for the estimation of the spatial transform in act c). In a particularly preferred embodiment, the estimation of the spatial transform is based on the well-known thin-plate-spline model that takes into account the deformation of the anatomic structures in both images. However, other models can also be used for the spatial transform, such as an affine transform model.

In another embodiment of act d), respective extracted candidate calcified plaques are each assigned to a specific vessel that is the vessel having a second centerline to which most of the image elements of the respective extracted candidate calcified plaque has the smallest distance. Here and in the following, the term "distance of an image element to a centerline" refers to the length of the shortest straight line between the image element and the centerline. In the case of 3D scans, an image element refers to a voxel, whereas an image element is a pixel in case of a 2D scan.

In another preferred embodiment of act d), candidate calcified plaques are also extracted from the first image, where the spatial transform in act c) is refined based on the positional differences between corresponding candidate calcified plaques in the first and the second images and where the method is continued based on the positional information of the second centerlines derived from the refined spatial transform. This embodiment enables a more accurate detection of calcified plaques.

In a particularly preferred embodiment, the above defined refinement of the spatial transform in act c) is such that the mean minimum distance between corresponding candidate calcified plaques in the first and the second images is minimized. The minimum distance is the smallest possible distance between an image element in the candidate calcified plaque of the first image and an image element in the candidate calcified plaque of the second image.

In a particularly preferred embodiment, the extraction of the candidate calcified plaques from the first image is only performed if a first condition is fulfilled. The first condition is preferably such that a number of extracted candidate calcified plaques in the second image exceeds a predetermined first threshold (e.g. 3).

In another preferred embodiment, the refinement of the spatial transform is only performed if a second condition is fulfilled. The second condition is preferably such that the number of extracted candidate calcified plaques in the first image exceeds a predetermined second threshold (e.g. 3).

In a particularly preferred variant, the machine learning classifier is a random forest classifier. Alternatively, other machine learning classifiers may be used, such as a support vector machine, a linear discriminant analysis, a logistic regression, or a probabilistic boosting tree.

In another preferred embodiment, the candidate calcified plaque extraction of act d) identifies as candidate calcified plaques in the second image groups of adjacent image elements in which each image element has a radio density exceeding a predetermined value. The radio density is a well-known quantity detected for image elements in medical images. It is usually measured in Hounsfield units abbreviated as HU.

In order to reduce the number of false positive candidate calcified plaques in the second image, the identification of the groups of adjacent image elements is a provisional identification that is discarded if at least one condition out of a number of conditions is fulfilled. The number of conditions includes one or more of the following conditions:
- all image elements in the group of adjacent image elements are outside a predefined anatomic structure in the second image, particularly outside the pericardium;
- the number of image elements in the group of adjacent image elements is less than a predetermined value (e.g. 3);
- the mean distance of the image elements in the group of adjacent image elements to the second centerlines is higher than a predetermined threshold (e.g. 15 mm);
- all image elements in the group of adjacent image elements are inside a predefined anatomic structure in the second image, particularly inside the aortic root;
- the maximum radio density of the image elements in the group of adjacent image elements in the second image is less than a predetermined value (e.g. 140 HU);
- the mean radio density difference between the image elements in the group of adjacent image elements and the image elements in a predefined neighborhood around the group of adjacent image elements is higher than a predetermined threshold (e.g. 90 HU).

The above mentioned predefined neighborhood is preferably defined such that this neighborhood includes a predefined number of adjacent pixels around the group of adjacent image elements.

In case that the extraction act d) uses the positional information of the second centerlines, the above defined mean distance to the second centerlines is used as the positional information in a preferred variant of the invention.

In another preferred embodiment, the number of features processed in act e) includes one or more of the following features and particularly all of the following features:
- the number of image elements in the respective candidate calcified plaque;
- the mean radio density of the image elements in the respective candidate calcified plaque;
- the maximum radio density of the image elements in the respective candidate calcified plaque;
- the number of image elements in the respective candidate calcified plaque above one or more threshold radio density values;
- the number of image elements in the respective candidate calcified plaque above one or more threshold radio density values normalized by the number of image elements in the respective candidate calcified plaque;
- the mean radio density of the image elements in a predefined neighborhood around the respective candidate calcified plaque;
- the maximum radio density of the image elements in a predefined neighborhood around the respective candidate calcified plaque;
- the radio density standard deviation of the image elements in a predefined neighborhood around the respective candidate calcified plaque;
- the difference between the mean radio density of the image elements in the respective candidate calcified plaque and the mean radio density of the image elements in a predefined neighborhood around the respective candidate calcified plaque;
- the difference between a first value and a second value, the first value being the difference between the mean radio density of the image elements in the respective candidate calcified plaque and the mean radio density of the image elements in a predefined neighborhood around the respective candidate calcified plaque and the second value being the radio density standard deviation of the image elements in a predefined neighborhood around the respective candidate calcified plaque;
- one or more statistical values referring to the distances of respective image elements in the respective candidate calcified plaque to the closest point of the second centerlines in the second image, the closest point being the point closest to the respective image element;
- the center of gravity of the respective candidate calcified plaque in on or more coordinate systems.

As mentioned before, the predefined neighborhood preferably refers to a predefined number of adjacent pixels around the respective candidate calcified plaque. In case that act e) uses the positional information of the second centerlines, one or more of the above features processing second centerlines are used in a preferred embodiment of the invention. Important features are also the above defined difference between the mean radio density of the image elements in the respective candidate calcified plaque and the mean radio density of the image elements in a predefined neighborhood as well as the above difference between the first value and the second value.

In a particularly preferred variant, the one or more statistical values referring to the distances of image elements in the respective candidate calcified plaque to the closest point of the second centerlines in the second image include one or more of the following values:
- the mean of the distances;
- the standard deviation of the distances;
- the maximum of the distances;
- the median of the distances;
- the mean absolute deviation of the distances from the median of the distances.

Besides the above method, a corresponding apparatus for computer-aided analysis of medical images is provided. The apparatus analyses a pair of medical images, the pair including a first image which is a contrasted scan of a part of a human or animal body and a second image which is a native scan of the same part of a human or animal body. This apparatus includes a processor configured to:

perform an act a) that is an act of identifying one or more anatomic structures within both the first image and the second image, resulting in a positional information of the one or more anatomic structure in the first and second images;

perform an act b) that is an act of identifying first centerlines of vessels in the first image, resulting in a positional information of the first centerlines in the first image;

perform an act c) that is an act of identifying second centerlines of vessels in the second image corresponding to respective first centerlines in the first image, resulting in a positional information of the second centerlines in the second image, where the identification of the second centerlines comprises the step of mapping the first centerlines from the first image to the second image by estimating a spatial transform from the first image to the second image based on the identified one or more anatomic structures in the first and second images;

perform an act d) that is an act of extracting candidate calcified plaques in the second image;

perform an act e) that is an act of identifying calcified plaques out of the candidate calcified plaques by a machine learning classifier processing a number of features of the candidate calcified plaques;

wherein performing act d) and/or the act e) is configured to use the positional information of the second centerlines in the second image.

The above apparatus is preferably configured to perform one or more preferred variants of the method.

A computer program product directly loadable into the internal memory of a digital computer may be provided. The product includes a program code performing the method or one or more preferred embodiments of the method, when the program code is run on a computer.

Moreover, a computer program includes a program code for performing the method or one or more preferred embodiment of the method, when the program code is run on a computer.

BRIEF DESCRIPTION OF THE DRAWINGS

Embodiments will now be described with respect to accompanying drawings wherein.

DETAILED DESCRIPTION OF THE EMBODIMENTS

In the following, the embodiments will be described based on medical images in the form of 3D scans of a human heart. It is the aim to identify calcified plaques in coronary vessels in the human heart based on both a native (non-contrasted) CT scan and a contrasted CT scan. The contrasted CT scan corresponds to an embodiment of a first image and the native CT scan corresponds to an embodiment of a second image as defined in the patent claims.

Figure 1:
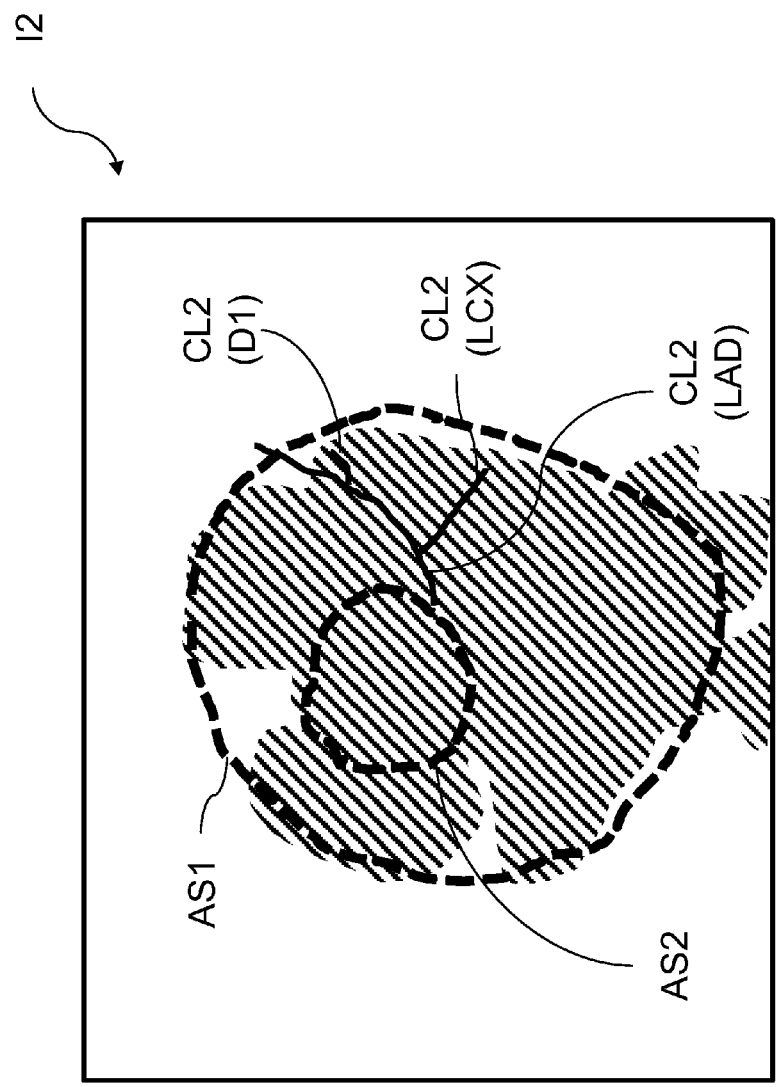
FIG. 1 is a schematic view of an example native CT scan of a human heart processed.
Figure 2:
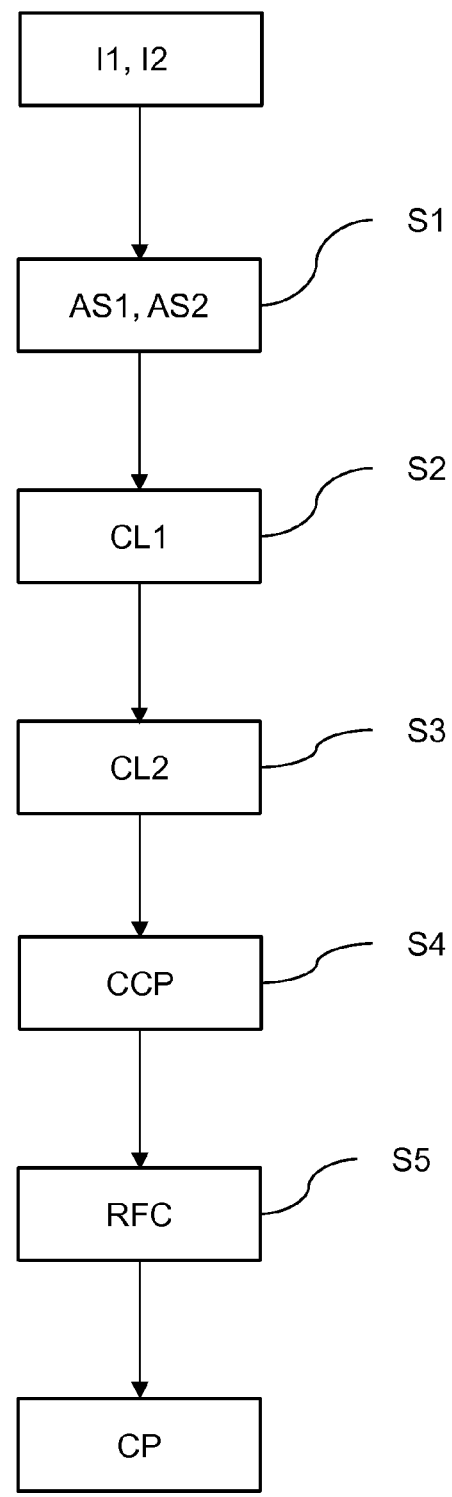
FIG. 2 is a flow chart illustrating the acts performed in an embodiment.

FIG. 1 is a schematic illustration of a two-dimensional slice of a native 3D CT scan processed in the embodiment described herein. The native CT scan is referenced as image I2. The hatched structure in FIG. 1 illustrates the structure of a human heart. In the real visualization, this structure is an area of different gray levels which may also include white partitions. Furthermore, the background of the image I2 is substantially black in the real visualization. The corresponding contrasted CT scan named as image I1 in FIG. 2 is not shown separately but it has a similar structure as the scan of FIG. 1. However, the contrast is better making it easier to identify separate areas of the human heart as well as coronary arteries due to the use of a contrast agent.

The embodiments as described in the following are implemented as software in a computer and analyze both the contrasted and native CT scans I1 and I2 in order to identify calcified plaques in coronary arteries and to distinguish those calcified plaques from calcifications of bones, which may also be included in the CT scans. An automatic approach for identifying calcified plaques without human interaction is provided.

In the first act of this approach, an anatomic information in the form of anatomic structures is extracted from both the contrasted and the native scans I1, I2, which form the input of the method. This is indicated as act S1 in FIG. 2. In the embodiment described herein, a segmentation of the pericardium forming an anatomic structure in the sense of the patent claims is detected as the boundary AS1 (dashed line) in the native CT scan I1 of FIG. 1. Analogously, the aortic root, which is also an anatomic structure, is identified as boundary AS2 (dashed line) in the native CT scan I2 of FIG. 1. In the same way as in FIG. 1, corresponding anatomic structures in the form of the pericardium and the aortic root are identified in the contrasted CT scan I1. The segmentation of the pericardium and the aortic root is performed by a well-known prior art method. In the embodiment described herein, so-called marginal space learning (MSL) is used for segmentation. MSL is used to estimate the position, orientation and size of the heart. A mean shape, which is trained on a set of example shapes, is then aligned with the estimated pose as an initial estimate of the boundary of the pericardium and the aortic root. In the MSL method performed in this embodiment, learning-based boundary detectors are used to guide the boundary evolution under the well-known active shape model (ASM) framework. However, the sternum and ribs are often included in the automatically segmented pericardium mesh when applying ASM directly. To distinguish sternum and ribs from the pericardium and aortic root, a post-processing step is performed in order to explicitly segment these bones to avoid the interference with the calcium scoring for calcified plaques. In the embodiment described herein, a post-processing step, such as disclosed in Zheng, Y., Vega-Higuera, F., Zhou, S. k., Comaniciu, D.: Fast and automatic heart isolation in 3D CT volumes: Optimal shape initialization. In: Proc. Intl. Workshop on Machine Learning in Medical Imaging (In conjunction with MICCAI) (2010) is implemented in the analyzing method.

In a next act named as S2 in FIG. 2, centerlines for the coronary artery tree are automatically extracted from the contrasted CT scan. The extraction may be as taught in Zheng, Y., Tek, H., Funka-Lea, G.: Robust and accurate coronary artery centerline extraction in CTA by combining model-driven and data-driven approaches. In: Proc. MICCAI (2013). A learning based verification act, such as described in Kelm, B., Mittal, S., Zheng, Y., Tsymbal, A., Dominik, Vega-Higuera, F., Zhou, S., Meer, P., Comaniciu, D.: Detection, grading and classification of coronary stenosis in computed tomography angiography. In: Proc. MICCAI (2011), corrects for vessel tree parts erroneously traced into non-vessel structures. As a result of act S2, coronary centerlines forming the coronary centerline tree are identified in the contrasted CT scan I1. Those coronary centerlines are named as CL1 in FIG. 2.

In the next step S3 of FIG. 2, the coronary centerlines CL1 are mapped from the contrasted scan I1 to the native scan I2 based on the segmented pericardium meshes and the overlapping parts of the aortic root (starting from the hinges). In other words, a spatial transform from the contrasted CT scan to the native CT scan is estimated in order to identify the coronary centerlines as extracted in the contrasted scan in the corresponding native scan. Point correspondences between the segmentation meshes of the native and the contrasted scan can be assumed since a model-based approach (ASM) has been used. In the embodiment described herein, the well-known thin-plate-spline (TPS) model is used for estimating the spatial transform. This model interpolates the deformation field within the pericardium. However, other point-based registration (mapping) methods (rigid as well as deformable) could be applied. Nevertheless, the TPS model has the advantages that the interpolation is smooth with derivatives of any order and that the model has no free parameters that need manual tuning and that it has closed-form solutions for both warping and parameter estimation.

As a result of the mapping act S3, centerlines CL2 of coronary arteries are identified in the native CT scan. Those centerlines CL2 are illustrated as solid lines in the native CT scan as shown in FIG. 1. The identified centerlines refer to different arteries in the human heart, namely the left anterior descending LAD, the first diagonal D1, and the left circumflex LCX. The assignment of those arteries to the centerlines is indicated in FIG. 1 by corresponding reference numerals in brackets.

In the next act S4, candidate calcified plaques CCP are extracted in the native scan I2. To do so, the radio densities (also named as intensities in the following) in Hounsfield units (HU) of three-dimensional voxels in the 3D native scan are processed. Particularly, connected groups of voxels (3D 6-connectivity), i.e. voxels having at least one common boundary point, with intensities above $t_{cal}$=130 HU are identified as possible candidate calcified plaques. However, additional constrains are imposed taking into account the centerlines CL2 in the native CT scan. This was done in order to reduce the number of (false positive) candidates. In other words, a possible CCP is discarded as a CCP if at least one of the following conditions is fulfilled:
1. All voxels of a respective connected group are outside the pericardium.
2. The number of voxels in the respective connected group is less than n=3.
3. The mean distance of the voxels in the respective connected group to the coronaries (i.e. to the centerlines CL2) is more that $d_v$=15 mm.
4. All voxels in the respective connected group are within the aortic root.
5. The maximum intensity of the voxels in the respective connected group is less than $I_{max}$=140 HU.
6. The mean intensity difference to the surrounding tissue of the respective connected group is less than $D_{max}$=90 HU.

Here and in the following, the term "distance of a voxel to a coronary/centerline" refers to the length of the shortest straight line between the voxel and the coronary/centerline. The intensity of the surrounding tissue is computed as the mean intensities of 100 voxels around the possible calcified plaque CCP. Finally, the extracted CCPs are labeled as belonging to the type of vessel to which most of its voxels are closest.

In a modification of the extraction act described above, the CCPs are also extracted from the contrasted scan if the number of CCPs extracted from the native scan in step S4 exceeds a certain number (e.g. $N_{CCP}$=3). To do so, different from the native scan, the intensity threshold $t_{cal}$ for calcification is adjusted to the lumen intensity in the contrasted scan. The intensity is close to that of calcium due to the injected contract agent. To this end, the mean plum and standard deviation alum of the lumen intensity are estimated from voxels within the segmented ascending aorta, where a small border to the aortic wall is kept to exclude potential calcifications. Based on these, a calcification threshold of $t_{cal}=\mu_{lum}$+1.2 alum is used for CCP extraction. Furthermore, of the six constraints listed above, only the first three are applied to CCPs from the contrasted scans. However, the third constraint is modified in that the mean distance to the closest calcified centerline point should not exceed $d_v$=10 mm, where calcified centerline points are identified by the calcification detector, such as described in Isgum, I., Rutten, M., Prokop, M., van Ginneken, B.: Detection of coronary calcifications from computed tomography scans for automated risk assessment of coronary artery disease. Medical Physics 34(4), S. 1450-1461 (2007).

If the number of CCPs extracted from the contrasted scan again exceeds $N_{CCP}$, the registration (mapping) between the contrasted and native scan is refined. To do so, the translational part of the spatial transform estimated in act S3 is adjusted as to minimize the mean minimum distance between the CCPs of the native and the contrasted scans. The refined spatial transform leads to new positions of centerlines CL2. Based on these new positions, the extraction of calcified plaques is repeated in act S4, resulting in new CCPs which are then labeled as belonging to the type of vessel to which most of its voxels are closest, as it is the case in the previously described variant of the method.

In a next act S5, a machine learning classifier trained by corresponding training data is used in order to distinguish between true positive and false positive CCPs as extracted in act S4. In the embodiment described herein, the so-called random forest classifier RFC is applied. The random forest classifier is an ensemble learning method that operates by constructing a multitude of decision trees at training time and outputting the class based on the rate of the classifications of all individual decision trees (e.g., particularly based on the majority vote). During training, a predetermined number of observations in the training data are sampled, with replacement. Furthermore, a number of randomly selected features of the observations are used at each node (i.e. at each split in the decision trees) when learning the individual tree. As the random forest classifier is well-known in the prior art, a detailed description of this classifier is omitted.

In the embodiment described herein, a total of 36 features as listed in the following Table 1 are used for training and applying the random forest classifier. The classifier was tested with different probability thresholds. In case that the rate of the classifications of all individual decision trees in the class "calcified plaque" (out of the classes "calcified plaque" and "not being a calcified plaque") exceeds the predetermined threshold, the candidate calcified plaque is regarded as a calcified plaque. The results presented in the following are based on a probability threshold of 0.5.

TABLE 1

| name | parameter range | description |
|---|---|---|
| size | — | number of voxels |
| meangray | — | mean intensity |
| maxgray | — | maximum intensity |
| ccnt<n> | <n> = 134:4:166 | number of voxels above <n> Hounsfield units |
| chist<n> | <n> = 134:4:166 | ccnt<n> normalized by the number of voxels |
| lmeangray | — | mean intensity of voxels in local neighborhood |
| lmaxgray | — | maximum intensity of voxels in local neighborhood |
| lstdgray | — | intensity standard deviation in local neighborhood |
| ldgray | — | meangray - lmeangray |
| lddgray | — | ldgray - lstdgray |
| vdist_<t> | <t> ∈ {mean, std, max, median, mad} | statistics of the voxel distances to the closest centerline point |
| cog_<t> | ⟨t⟩ ∈ {x, y, z} | center of gravity relative to the pericardium |
| cog_<t> | ⟨t⟩ ∈ {sin, cos} | center of gravity in cylindrical coordinates |

In the above table, the features refer to the voxels within a corresponding extracted CCP. The term "local neighborhood" in the table refers to a predefined number of adjacent voxels (e.g. 100 voxels) around the candidate calcified plaque. Moreover, the expression <n>=134:4:166 in the above table indicates that, as thresholds for the Hounsfield units, numbers of voxels between 134 and 166, subsequently being incremented by four, are used. Furthermore, the following abbreviations apply in the above table:
mean=the mean of the voxel distances;
std=standard deviation of the voxel distances;
max=maximum of the voxel distances;
median=the median of the voxel distances;
mad=median absolute deviation of the voxel distances from the median of the distances.

Summarized, for each candidate calcified plaque, the above features of Table 1 are input in the random forest classifier, which outputs as a result whether the candidate classified plaque can be identified as a calcified plaque CP within a vessel or not. The calcified plaques CP identified by the random forest classifier RFC in act S5 are eventually output by the analyzing method, as indicated in FIG. 2.

The above described analyzing method was tested based on native and contrasted scans for 64 patients. These were equally divided into a training (32) and a testing (32) set, each of which contains respectively 8 patients acquired on CT scanners from four different vendors. For the training set, also ground truth annotations (i.e. the correct classification as calcified plaque or not) were provided. The random forest classifier has been trained in a leave-one-patient-out (LOPO) fashion. For evaluation, the well-known sensitivity SENS and the positive predictive value PPV have been computed on a voxel-wise basis as well as on a lesion-wise basis. Using the voxel-wise basis, the correct classification of each voxel is checked. When using the lesion-wise basis, the correct classification of extracted candidate calcified plaques as a whole is checked. Moreover, the well-known interclass correlation coefficient ICC for the Agatston score is computed on the ground true and the automatic detections respectively. The Agatston score is a well-known quantity describing the degree of coronary calcification. Furthermore, the number of true positives TP, false negatives FN and false positives FP has been calculated for the lesion-wise evaluation. The method performs the better, the closer the respective values SENS, PPV and ICC are to 100% or 1.0. The results for the tested method are shown in the following Table 2.

TABLE 2

| voxel-wise | | lesion-wise | | | Agatston |
|---|---|---|---|---|---|
| SENS | PPV | SENS | PPV | TP/FN/FP | ICC |
| 96.12% | 90.71% | 85.33% | 91.28% | 157/27/15 | 0.968 |

Evidently, all values are close to the optimum value of 100% or 1.0. Hence, the analysis method provides a very accurate detection of calcified plaques in coronary vessels.

The embodiments as described in the foregoing have a number of advantages. Particularly, a fully automatic detection for coronary vessels is provided that does not need human interactions. By using the coronary vessel tree estimated from a contrasted scan, the individual vessels can be localized much more accurately in the native scan than by using a general, patient-independent prior. Furthermore, calcifications identified in both scans can be optionally used to further improve this accuracy. The mapping of the contrasted and native scans based on segmented anatomic structures is very fast in comparison to image-based registration. Due to the fully automatic approach, the physician can safe time for analyzing CT scans.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for computer-aided analysis of medical images, where a pair of medical images is analysed, the pair including a first image, which is a contrasted scan of a part in a human or animal body, and a second image, which is a native scan of the same part of the human or animal body, the method comprising:
   a) identifying one or more anatomic structures within both the first image and the second image, resulting in a positional information of the one or more anatomic structures in the first and second images;
   b) identifying first centerlines of vessels in the first image, resulting in a positional information of the first centerlines in the first image;
   c) identifying second centerlines of vessels in the second image corresponding to respective first centerlines in the first image, resulting in a positional information of the second centerlines in the second image, where the identification of the second centerlines comprises mapping the first centerlines from the first image to the second image by estimating a spatial transform from the first image to the second image based on the identified one or more anatomic structures in the first and second images;

d) extracting candidate calcified plaques in the second image;

e) identifying calcified plaques out of the candidate calcified plaques by a machine learning classifier processing a number of features of the candidate calcified plaques;

wherein d) and/or e) uses the positional information of the second centerlines in the second image.

2. The method according to claim 1, wherein the medical images are three-dimensional scans, CT scans, or three-dimensional CT scans.

3. The method according to claim 1, wherein the medical images are scans of a human or animal heart wherein the identified first and second centerlines of vessels refer to coronary arteries.

4. The method according to claim 3, wherein the identified one or more anatomic structures comprise the pericardium, the aortic root, or the pericardium and the aortic root in the human or animal heart.

5. The method according to claim 1, wherein marginal space learning is used in a) for identifying the one or more anatomic structures in the first and second images.

6. The method according to claim 1, wherein the estimation of the spatial transform in step c) is based on the thin-plate-spline model or an affine transform model.

7. The method according to claim 1, wherein in d) respective extracted candidate calcified plaques are each assigned to a specific vessel, which is the vessel having a second centerline to which most of the image elements of the respective extracted candidate calcified plaque have the smallest distance.

8. The method according to claim 1, wherein in d), the candidate calcified plaques are also extracted from the first image, where the spatial transform in c) is refined based on the positional differences between corresponding candidate calcified plaques in the first and the second images and where the method is continued based on the positional information of the second centerlines derived from the refined spatial transform.

9. The method according to claim 8, wherein the refinement of the spatial transform in c) is such that the mean minimum distance between corresponding candidate calcified plaques in the first and the second images is minimized.

10. The method according to claim 8, wherein the extraction of the candidate calcified plaques from the first image is only performed if a first condition is fulfilled, where the first condition is preferably such that the number of extracted candidate calcified plaques in the second image exceeds a predetermined first threshold.

11. The method according to claim 8, wherein the refinement of the spatial transform is only performed when a second condition is fulfilled, where the second condition is such the number of extracted candidate calcified plaques in the first image exceeds a predetermined second threshold.

12. The method according to claim 1, wherein the machine learning classifier is a random forest classifier, a support vector machine, a linear discriminant analysis, a logistic regression, or a probabilistic boosting tree.

13. The method according to claim 1, wherein the candidate calcified plaque extraction of d) identifies as candidate calcified plaques in the second image groups of adjacent image elements in which each image element has a radio density exceeding a predetermined value.

14. The method according to claim 13, wherein the identification of the groups of adjacent image elements is a provisional identification that is discarded when at least one condition out of a number of conditions is fulfilled, where the number of conditions comprises one or more of the following conditions:

all image elements in the group of adjacent image elements are outside a predefined anatomic structure in the second image;

the number of image elements in the group of adjacent image elements is less than a predetermined value;

the mean distance of the image elements in the group of adjacent image elements to the second centerlines is higher than a predetermined threshold;

all image elements in the group of adjacent image elements is inside a predefined anatomic structure in the second image;

the maximum radio density of the image elements in the group of adjacent image elements is less than a predetermined value; or the mean radio density difference between the image elements in the group of adjacent image elements and the image elements in a predefined neighborhood around the group of adjacent image elements is higher than a predetermined threshold.

15. The method according to claim 1, wherein the number of features processed in e) comprises one of more of the following features:

a number of image elements in the respective candidate calcified plaque;

the mean radio density of the image elements in the respective candidate calcified plaque;

the maximum radio density of the image elements in the respective candidate calcified plaque;

the number of image elements in the respective candidate calcified plaque above one or more threshold radio density values;

the number of image elements in the respective candidate calcified plaque above one or more threshold radio density values normalized by the number of image elements in the respective candidate calcified plaque;

the mean radio density of the image elements in a predefined neighborhood around the respective candidate calcified plaque;

the maximum radio density of the image elements in a predefined neighborhood around the respective candidate calcified plaque;

the radio density standard deviation of the image elements in a predefined neighborhood around the respective candidate calcified plaque;

the difference between the mean radio density of the image elements in the respective candidate calcified plaque (CCP) and the mean radio density of the image elements in a predefined neighborhood around the respective candidate calcified plaque;

the difference between a first value and a second value, the first value being the difference between the mean radio density of the image elements in the respective candidate calcified plaque and the mean radio density of the image elements in a predefined neighborhood around the respective candidate calcified plaque and the second value being the radio density standard deviation of the image elements in a predefined neighborhood around the respective candidate calcified plaque;

one or more statistical values referring to the distances of respective image elements in the respective candidate calcified plaque to the closest point of the second centerlines in the second image, the closest point being the point closest to the respective image element; or the center of gravity of the respective candidate calcified plaque in on or more coordinate systems.

16. The method according to claim 15, wherein the one or more statistical values referring to the distances of image elements in the respective candidate calcified plaque to the closest point of the second centerlines (in the second image comprise one or more of the following values:

the mean of the distances;

the standard deviation of the distances;

the maximum of the distances;

the median of the distances; or the median absolute deviation of the distances from the median of the distances.

17. An apparatus for computer-aided analysis of medical images, where a pair of medical images is analysed, the pair including a first image, which is a contrasted scan of a part in a human or animal body, and a second image, which is a native scan of the same part of the human or animal body, the apparatus comprising:

a processor configured by instructions to:

identify one or more anatomic structures within both the first image and the second image, resulting in a positional information of the one or more anatomic structure in the first and second images;

identify first centerlines of vessels in the first image, resulting in a positional information of the first centerlines in the first image;

identify second centerlines of vessels in the second image corresponding to respective first centerlines in the first image, resulting in a positional information of the second centerlines in the second image, where the identification of the second centerlines comprises the step of mapping the first centerlines from the first image to the second image by estimating a spatial transform from the first image to the second image based on the identified one or more anatomic structures in the first and second images;

extract candidate calcified plaques in the second image;

identify calcified plaques out of the candidate calcified plaques by a machine learning classifier processing a number of features of the candidate calcified plaques;

wherein extracting the candidate calcified plaques, identifying the calcified plaques or both use the positional information of the second centerlines in the second image.

18. The apparatus according to claim 17, wherein the processor is configured to identify the one or more anatomic structures with marginal space learning.

19. The apparatus according to claim 17, wherein the processor is configured to also extract the candidate calcified plaques from the first image, where the spatial transform is refined based on the positional differences between corresponding candidate calcified plaques in the first and the second images and where the positional information of the second centerlines is derived from the refined spatial transform.

20. The apparatus according to claim 17, wherein the processor is configured to identify as the candidate calcified plaques in the second image groups of adjacent image elements in which each image element has a radio density exceeding a predetermined value.

* * * * *